United States Patent
Howe et al.

(10) Patent No.: US 9,724,281 B2
(45) Date of Patent: Aug. 8, 2017

(54) COMPOSITION OF RESVERATROL AND METHOD FOR ITS USE IN THE TREATMENT OF SKIN CONDITIONS

(71) Applicants: Bruce L. Howe, San Diego, CA (US); Kodimule Shyam Prasad, Bangalore (IN)

(72) Inventors: Bruce L. Howe, San Diego, CA (US); Kodimule Shyam Prasad, Bangalore (IN)

(*) Notice: Subject to any disclaimer, the term of this patent is extended or adjusted under 35 U.S.C. 154(b) by 0 days.

(21) Appl. No.: 15/000,943

(22) Filed: Jan. 19, 2016

(65) Prior Publication Data

US 2016/0213584 A1 Jul. 28, 2016

Related U.S. Application Data

(60) Provisional application No. 62/105,218, filed on Jan. 20, 2015.

(51) Int. Cl.

| | |
|---|---|
| *A61K 8/34* | (2006.01) |
| *A61Q 19/08* | (2006.01) |
| *A61Q 19/02* | (2006.01) |
| *A61K 8/55* | (2006.01) |
| *A61K 8/92* | (2006.01) |
| *A61K 31/05* | (2006.01) |

(52) U.S. Cl.
CPC ............ *A61K 8/347* (2013.01); *A61K 8/553* (2013.01); *A61K 8/922* (2013.01); *A61K 31/05* (2013.01); *A61Q 19/08* (2013.01); *A61Q 19/02* (2013.01)

(58) Field of Classification Search
None
See application file for complete search history.

(56) References Cited

U.S. PATENT DOCUMENTS

| | | | | |
|---|---|---|---|---|
| 5,629,015 A | * | 5/1997 | Ribier | A61K 8/14 424/401 |
| 6,045,779 A | * | 4/2000 | Mueller | A61K 8/604 132/202 |
| 2011/0009496 A1 | * | 1/2011 | Lunsmann | A61K 9/08 514/729 |
| 2011/0281957 A1 | * | 11/2011 | Kuhrts | A61K 9/06 514/733 |
| 2012/0064136 A1 | * | 3/2012 | Baker, Jr. | A61K 8/06 424/401 |

FOREIGN PATENT DOCUMENTS

WO  WO2009029887  * 3/2009

* cited by examiner

*Primary Examiner* — Jianfeng Song
(74) *Attorney, Agent, or Firm* — Law Office of Timothy M. Brown

(57) ABSTRACT

Compositions of resveratrol having enhanced properties. The compositions of the invention can comprise resveratrol and one or more agents that increase the bioavailability, efficacy and/or bioactivity of the resveratrol. Compositions of the invention find use in the treatment of a variety of conditions, including skin conditions and preventative health maintenance. Methods of making the inventive compositions are also contemplated.

13 Claims, 4 Drawing Sheets

COMPOSITION OF RESVERATROL AND METHOD FOR ITS USE IN THE TREATMENT OF SKIN CONDITIONS

CROSS-REFERENCE TO RELATED APPLICATIONS

This application claims priority to Provisional Application Ser. No. 62/105,218 filed Jan. 20, 2015, the entire disclosure of which is incorporated by reference herein in its entirety for all purposes.

FIELD OF THE INVENTION

The invention relates to neutraceutical compositions with increased beneficial properties, and methods for making and using such compositions. More particularly, the invention provides compositions comprising resveratrol with increased bioactivity, bioavailability, and/or efficacy, and methods of making and using such compositions in health maintenance and the treatment of conditions and disorders.

BACKGROUND

Resveratrol, also known as 3,5,4'-trihydroxystilbene, is a stilbene found in grape skin. Resveratrol, a non-flavonoid polyphenolic antioxidant, is one of the widely studied phytochemicals with demonstrated health potential due to its antioxidant, anticancer, and anti-inflammatory properties (Athar et al. 2007; Shankar et al. 2007). It is best known for being found in high concentrations in red wine, but is also present in very small amounts in many other plant products (Bielsalski, 2007). While resveratrol is often reported to be present in peanuts (a maximum of 1.92 µg/g) and other plant products, the amount is almost negligible compared to that in wines. One notable exception to this is the herb *Polygonum Cuspidatum* which has a resveratrol concentration of 0.524 mg/g.

Interest in resveratrol has been renewed in recent years, first from its identification as a chemo preventive agent for skin cancer, and subsequently from reports that it activates sirtuindeacetylases and extends the lifespan of lower organisms. Despite skepticism concerning its bioavailability, a growing body of in vivo evidence indicates that resveratrol has protective effects in rodent models of stress and disease. In particular, the present invention relates to compositions and methods for supplementation of resveratrol from *P. cuspidatum* with bioenhancers to increase the bioavailability of resveratrol and the use of such compositions in the treatment of skin conditions. In one aspect of the invention, the bioenhancers include sunflower lecithin and grape seed oil.

Skin aging is a multisystem degenerative process that involves the skin and the skin support system (Sjerobabski & Poduje, 2008). The process of skin aging may be divided as intrinsic and extrinsic aging (Jenkins, 2002; Schlotmann et al. 2001). It may be caused by several factors, such as, UV irradiation, stress, ROS generation or smoking. Wrinkle formation is a striking feature of photo-aged skin and is caused by the degradation of collagen fibrils and gelatin fibers. Further, because of increased melanin synthesis, the hyper-pigmented skin is observed in various dermatological disorders namely melasoma, solar lentigines and ephilides. These clinical conditions are due to frequent exposure to UV rays, certain drugs and chemicals resulting in skin darkening. Depigmenting agents commonly are prescribed to treat such disorders. The most common skin lightening and depigmentation agents available commercially include arbutin, catechins, hydroquinone and azelaic acid (Maeda & Fukuda, 1996). Some adverse effects of these synthetic compounds are irreversible cutaneous damage, ochronosis etc. These adverse effects have led to the search for safer, plant-based skin lightening ingredients.

DEFINITIONS

As used herein, the term "bioenhancer" refers to a substance that increases the bioactivity, bioavailability, and/or efficacy of another substance. The term "bioenhancer" includes, but is not limited to, a substance that increases another's substance's ability to modulate (e.g. inhibit or increase) the activity of a biomolecule. A "bioenhanced" substance refers to a substance that has been treated (e.g. contacted, formulated, mixed, or combined) with an amount of at least one bioenhancer sufficient to increase the bioactivity, bioavailability, and/or efficacy of the treated substance.

As used herein, the phrase "comestible oil" refers to a non-toxic, edible oil that may be consumed by a mammal and combined with resveratrol as disclosed herein. Examples of comestible oils include, but are not limited to, grape seed oil, jojoba oil, soybean oil, almond oil, avocado oil, petrolatum oil, vegetable oil, peanut oil, canola oil, flax seed oil, palm kernel oil, coconut oil, olive oil, or a combination thereof.

As used herein, the term "bioactivity" refers any type of interaction of a substance with a biomolecule, such biomolecules including, but not limited to, proteins, amino acids, glycoproteins, carbohydrates, oligosaccharides, polysaccharides, nucleotides, polynucleotides, fatty acids, hormones, lipids, phospholipids, enzymes, cofactors or the like, whether the interactions involve covalent or noncovalent binding. Bioactivity further includes interactions of substances with any type other cellular components or constituents including salts, ions, metals, nutrients, foreign or exogenous agents present in a cell (e.g. prokaryote or eukaryote cell) or virus, for example by binding, sequestration or transport-related interactions.

As used herein, the term "bioavailability" refers to the availability, amount (e.g., concentration), or pharmacological activity of a substance in the biological fluid, cells, or tissues (e.g. blood, serum, cerebrospinal fluid, skin, or brain) of a subject. As used herein, the term "enhancing the bioavailability" of a substance includes, but is not limited to, increasing or improving the bioavailability of a substance through the use of a bioenhancer relative to the bioavailability of the substance in the absence of the bioenhancer. Increased or enhanced bioavailability can be achieved by, for example, increasing or enhancing the concentration or rate of activity of a substance in the targeted biological fluid, cell, or tissue through the use of the bioenhancer.

As used herein, the term "increase," or "enhance." refers to any measurable increase in a target parameter that results from a given set of conditions (e.g. treatment of a substance with at least one bioenhancer) relative to the absence of such conditions.

As used herein, the term "purified" refers to a substance that is at least 75%, 85%, 90%, 95%, 100% free of any other substance, including any percentage that intervenes such specifically listed percentages.

As used herein, the term "about" means greater or lesser than the value or range of values stated by $1/10$ of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values.

The term "treatment," "treat," "treating," and the like refer to any treatment of a condition, disease or disorder, and includes: (1) preventing the disease or condition from occurring in a subject which may be predisposed to the disease but has not yet been diagnosed as having it. (2) inhibiting the disease or condition, i.e., arresting its development. (3) relieving the disease or condition, i.e., causing regression of the condition, or (4) relieving the conditions caused by the disease or condition, i.e., stopping, decreasing or reversing the symptoms of the disease or condition.

The term "subject" as used herein refers to the individual that receives the administration of an agent, including but not limited to the compositions of the invention, in the treatment of a targeted condition, disease or disorder. Subjects include, but are not limited to, mammals such as humans, livestock (e.g. sheep, cattle, horses, goats, pigs, and poultry), for example. Subjects include, but are not limited to, animals used in scientific research (e.g. mice and rats).

DESCRIPTION

The invention generally relates to neutriceutical compositions having increased bioactivity. More particularly, the invention relates to compositions comprising resveratrol and at least one bioenhancer, and methods for making and using such compositions in nutrition, health maintenance and the treatment of diseases, disorders and conditions.

In some aspects, the invention is a composition comprising resveratrol and one or more bioenhancers. Suitable sources of resveratrol include, but are not limited to resveratrol derived from natural sources such as grape skins, wine, or other botanical sources such as *P. cuspidatum* or *C. quinquangulata*, or produced synthetically such as 98% trans-resveratrol, available commercially from Sigma Chemical Co., St. Louis. Mo. Reseveratrol for use in the compositions can be trans-resveratrol, cis-resveratrol, or a combination thereof. Botanical extracts with higher concentrations of resveratrol may be produced by fractionation and further column chromatography until an extract containing up to a 99% concentration of resveratrol (e.g. as a mixture of both cis- and trans-resveratrol) is produced. The compositions of the invention may also be made using modified resveratrol or derivatives of resveratrol. Some non-limiting examples of resveratrols for making the compositions of the invention include, but are not limited to those disclosed in EP2774915, WO 2010062824, and WO 201006282, the disclosures of which are incorporated by reference in their entirety for all purposes.

In one aspect of the invention, resveratrol is contacted with (e.g. combined, blended or mixed) with one or more bioenhancers. Such bioenhancers may increase the bioavailability, bioactivity and/or efficacy of resveratrol. Some non-limiting examples of bioenhancers for combining with resveratrol include, but are not limited to, lecithin, piperine, garlic, lysergol, naringin, quercetin, niaziridin, glycyrrhizin, capsaicin, curcumin, ferulic acid and oils such as grape seed oil, peppermint oil, carrot oil, caraway oil, capmul, MCM C10, and combinations thereof. The bioenhancers disclosed herein may be used individually, or in combination with one another. In one non-limiting embodiment, resveratrol is combined with lecithin and/or grape seed oil.

One aspect of the invention relates to the amount of the one or more bioenhancers that are combined with resveratrol. In some embodiments, the compositions of the invention comprise at least, by weight, about 10%, 20%, 30%, 40%, 50%, 60%, 70%, 80%, 85%, 90%, 95%, 96%, 97%, 98%, or 99% resveratrol, as well as any percentage that intervenes these specifically listed percentages. In one non-limiting embodiment, the composition comprises about 98% resveratrol and about 2% of the at least one bioenhancer. In one non-limiting embodiment, the composition comprises about 98% resveratrol, 1% of one or more comestible oils, and 1% lecithin (e.g. sunflower lecithin). The components of the composition can be present in ratios with respect to one another. In one non-limiting embodiment, the compositions can comprise resveratrol and lecithin in a ratio of 49:1. The compositions can comprise resveratrol, lecithin and one or more comestible oils in a ratio of 98:1:1.

Some aspects of the invention concern formulating the composition for administration to a subject. Accordingly, the compositions of the invention may be formulated to be administered orally, sublingually, intranasally, topically, intravenously, intramuscularly, subcutaneously, buccally, parenterally, intravaginally, rectally, and by inhalation. The compositions may be in a dosage form that includes but is not limited to powders, pills, tablets, pellets, capsules, thin films, solutions, sprays, syrups, linctuses, lozenges, pastilles, chewing gums, pastes, vaporizers, suspensions, solutions, emulsions, ointments, creams, lotions, liniments, gels, drops, topical patches, buccal patches, beads, gummies, gels, sols, injections and the like. The composition may comprise at least one pharmaceutically acceptable excipient. Suitable excipients for use with the invention include, but are not limited to, those disclosed in Remington's Pharmaceutical Sciences, 18th ed. the disclosure of which is incorporated herein by reference in its entirety. The pharmaceutically acceptable excipient can an artificial pharmaceutical carrier. In some aspects of the invention, resveratrol is the only pharmaceutically active component in the composition.

An aspect of the invention relates to the format the composition assumes. Such formats will depend upon the particular bioenhancer(s) that are contacted with resveratrol, as well as the excipient and/or solution in which the compositions are formulated. The compositions of the invention may be in the form of a solution, emulsion, or suspension. In some aspects of the invention, the compositions are free of liposomes and/or micelles. In one non-limiting embodiment of the invention, the compositions of the invention comprise resveratrol, at least one comestible oil, and lecithin. In some aspects, the comestible oil can be grape seed oil. The compositions of the invention can be free of liposomes and/or micelles.

Some aspects of the invention relate to methods of using the compositions in applications where a subject (e.g. human subject) may benefit from the administration of resveratrol. Accordingly, the compositions may be administered, for example, as a means for protecting the cardiovascular system, potentiating the immune response, contrasting inflammatory ailments such as arthritis, pathogenic infections, aging, obesity and metabolic disease, improving skeletal muscle functionality and intellectual performance impaired by age or neurodegeneration, and preventing or contrasting cancer. The compositions may find extensive usage in the inhibition of numerous types of cancer including leukemias, multiple myeloma, melanoma, and cancers of breast, ovaries, prostate, stomach, colon, liver, pancreas, thyroid, uterine cervix. The compositions may be administered as tumor suppressor mediated through the regulation of various enzymes and molecules that regulate cellular reproduction and blood supply to the tumor. The compositions can be administered as an anti-inflammatory agent in the treatment of chronic arthritis by blocking the activity of compounds such as prostaglandins and cytokines. The compositions can be administered to protect the brain and nervous system against disorders associated with aging and genetic factors such as Alzheimer's disease and Huntington's disease. The compositions can be administered to control blood sugar levels in patients with diabetes and the reduction of hemoglobin A1c. The compositions can be administered to patients with cardiovascular disease including but not limited to myocardial infarction, the reduction of cholesterol, C-reactive protein and blood pressure. The compositions can be administered as an anti-obesity agent.

Some aspects of the invention relate to methods of using the compositions in the treatment of skin conditions. Such methods include administering the composition of the invention to a subject in need of treatment for a skin condition. Skin conditions as disclosed herein include, but are not limited to, wrinkles and fine lines, sagging skin, dryness, darkened skin (e.g. skin lightening), xerosis, itching, dermatitis, asteatotic eczema, atopic dermatitis, nummular dermatitis, hand dermatitis, dyshidrotic eczema, stasis dermatitis, seborrheic dermatitis, psoriasis, pityriasis, rosea, vitiligo, acne, lacerations, eczema, lymphoma of the skin. The compositions of the invention can be administered orally, sublingually, intranasally, topically, intravenously, intramuscularly, subcutaneously, buccally, parenterally, intravaginally, rectally, and by inhalation.

In some aspects of the invention, the compositions are administered to a subject in the treatment of wrinkles, fine lines, and/or loss of skin turgor. Without being limited to any particular theory, the compositions treat such conditions by inhibiting elastase. The compositions can be administered to a subject in an amount effective to inhibit elastase in the subject, wherein the degree of inhibition of elastase is sufficient to treat wrinkles, fine lines and/or skin turgor in the subject. In one non-limiting embodiment, a composition comprising resveratrol, lecithin, and grape seed oil is administered orally to a subject at a dosage of between about 50-500 mg, or topically at a dosage of between about 25-50 mg. The compositions of the invention can be administered one or multiple times, such as one or more times a day. The compositions of the invention can be administered, one, two, three, four, five, six, seven or more times per day.

In some aspects of the invention, the compositions are administered in order to lighten the color of the skin. Without being limited to any particular theory or mechanism, the compositions treat such conditions by inhibiting tyrosine. In one non-limiting embodiment of the invention, such compositions comprise resveratrol, lecithin, and grape seed oil and are administered orally at a dosage of about between about 50-500 mg, or topically at a dosage of between about 25-50 mg once, twice, three, four, five, six, seven or more times a day.

Example 1—Bioavailability of Bioenhanced Resveratrol Formulation

The purpose of this study was to evaluate the bioavailability of 50% resveratrol from *Polygonum cuspidatum* (RS) and its formulation with bioenhancers (1% sunflower lecithin and 1% grape seed oil) (RSF) via concentrations in rat plasma after oral administration.

Materials and Methods

Animal Treatment

Dosing formulations of resveratrol (RS) and resveratrol bioavailable form (RSF) were prepared for oral dosing formulations in a vehicle of 0.5% (w/v) aqueousmethylcellulose containing 0.2% (w/v) Tween 80; a dosing volume of 10 mL/kg bodyweight was used for gavage administration. All vehicle components were purchased from Sigma-Aldrich (St. Louis, Mo.).

Study Design and Conduct

At the end of the quarantine period, rats were randomly assigned to one of ten dosing groups using a computerized body weight stratification procedure that produced similar group mean body weight values. Body weights for the animals assigned to the study ranged from 201 to 241 g.

Detailed clinical and physical observations, including body weight collection, were performed on each surviving animal once during the quarantine period, and on Days 1, 8, and 14 of the treatment period. Food consumption was measured individually for each study animal in the repeat-dose groups on Days 8 and 14 of the treatment period.

In groups receiving a single dose of RS or RSF, blood samples were collected from three animals per group at 8 time points (oral dose groups); blood was collected at time 0 (predose), 1, 2, 4, 6, 8, 12, and 24 h after dose administration. Animals were anesthetized and blood samples (approximately 1 mL) were collected via retro-orbitalsinus puncture. The same schedule of blood collection was used after the final dose in animals receiving RS or RSF daily for 14 days.

Blood samples were collected in Vacutainer tubes (Fisher Scientific, Pittsburgh, Pa.) containing ethylenediaminetetraacetic acid (EDTA). Tubes were inverted several times to mix and were then placed on ice until centrifuged to separate plasma within 1 h time. After centrifugation, plasma was transferred into storage tubes (0.5 mL), which were stored frozen (approximately −70° C.) until analyzed.

Analytical Method

Plasma levels of resveratrol (RS) and resveratrol formulation (RSF) were measured using a tandem mass spectrometer equipped with a high performance liquid chromatograph (Agilent 1200; Agilent Technologies, Wilmington, Del.). For RS or RSF determination, a 100 μL aliquot of plasma was mixed with 1 mL of acetonitrile (ACN; Sigma-Aldrich, India). For resveratrol analysis, an internal standard resveratrol 13C6 (Toronto Research Chemicals, Inc., Ontario, Canada) was added at a concentration of 25 ng/mL. After vortex mixing for 1 min, the sample was centrifuged at 7,000 RPM at 4° C. for 10 min to remove precipitated proteins; the supernatant was transferred to a clean tube and dried under nitrogen at room temperature (approximately 25° C.). After the evaporation was completed, the residue was reconstituted in 100 μL of methanol with 5 min of sonication, added to 400 μL of water, vortex mixed, and centrifuged again. The resulting supernatant was transferred to a sample vial for instrumental analysis. All sample preparations were conducted under yellow light and using opaque plastic ware to avoid light exposure of the agent.

Freshly prepared RS standard curves were analyzed along with samples on each day of analysis. Instrument calibrators and quality control (QC) samples were prepared by adding 10 μL of a stock resveratrol or RSF solution (in a methanol/water mixture [v/v50:50] to 100 μL of rat plasma (Bioreclamation Inc., Westbury, N.Y.). Target calibrator concentrations were 5, 10, 20, 50, 100, 200, 500, and 1,000 ng/mL. QC samples were prepared at approximately 12, 400, and 800 ng/mL. Calibrators and QC samples were processed for analysis using the procedure described earlier. The concentration of conjugated metabolites for both agents was estimated using the calibration curve for each parent compound.

Chromatography was performed using a Luna 3μ C18, 30×2.0 mm column maintained at a temperature of 25° C. A flow rate of 0.25 mL/min was used. Mobile phase (MP) A consisted of 5 mM ammonium acetate in water:isopropanol (98:2, v/v); and MP B consisted of methanol:isopropanol (98:2, v/v). The MP gradient was as follows: after injection, initial conditions with MP A at 90% were held for 0.5 min, decreased to 5% in 3.5 min and held constant for 5 min, returning to initial conditions for another 3 min of re-equilibration time. Total run time was 12 min.

Pharmacokinetic Analysis

Mean plasma concentration-time profiles of RS and RSF in the rats at scheduled (nominal) sampling times were analyzed by noncompartmental pharmacokinetic methods using WinNonlin® Professional Edition software, Version 5.0.1 (Pharsight Corporation, Mountain View, Calif.).

Statistical Analysis

Mean, SD and RSD were determined by using Microsoft Excel and Win Nonlin software.

Results

Figure 1:
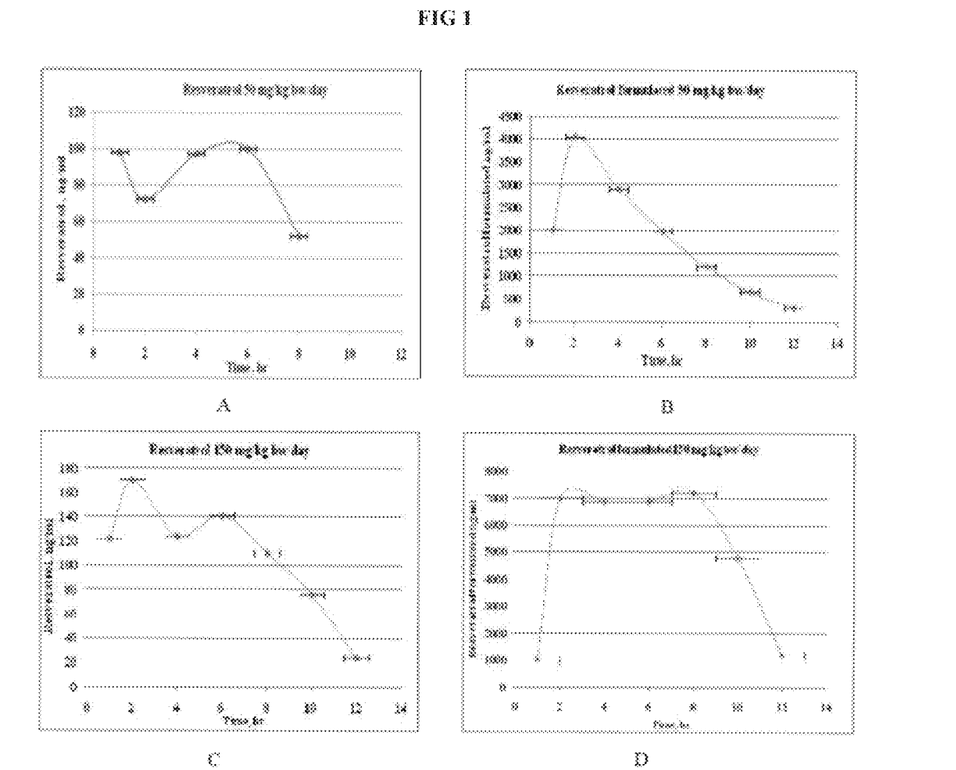
FIG. 1 shows plasma concentration time curves for resveratrol and bioenhanced resveratrol. Animals were orally dosed daily for 14 days, and pharmacokinetic profiles were obtained after the last dose. Symbols represent mean±SD for n=3.

Pharmacokinetic profiles of RS and RSF after 14 days of oral dosing are depicted in FIG. 1; similar results were seen in animals receiving a single oral dose (data not shown). After administration of equimolar doses, plasma concentrations of RSF were substantially greater than were plasma concentrations of RS at both dose levels evaluated in the study. The bioavailability of both RS and RSF appeared to be largely independent of the dose (over the 3-fold dose range used in the study); at both doses and durations of exposure, the bioavailability of RSF was approximately 3- to 4-fold greater than was the bioavailability of RS. This finding is consistent with much greater Cmax values for RSF (Table 1).

TABLE 1

Summary of pharmacokinetic parameters of 50% RS and RSF following daily oral dosing for 1 and 14 days.

| Chemical | Dose (mg/kg) | No. of doses | $T_{max}$ (h) | $C_{max}$ (ng/mL) |
|---|---|---|---|---|
| RS | 50 | 1 | 1 | 76.7 |
| RSF | 50 | 1 | 2 | 2,820 |
| RS | 50 | 14 | 6 | 176 |
| RSF | 50 | 14 | 2 | 4040 |
| RS | 150 | 1 | 1 | 847 |
| RSF | 150 | 1 | 4 | 7800 |
| RS | 150 | 14 | 2 | 484 |
| RSF | 150 | 14 | 8 | 7200 |

RS: 50% resveratrol from *P. cuspidatum*;
RSF: 50% resveratrol + 1% organic sunflower oil + 1% organic grape seed oil Example 2—Antioxidant Activity of Bioenhanced Resveratrol Formulation The aim of this study was to discuss the skincare benefits of a formulation of resveratrol in comparison with 50% resveratrol from *Polygonum cuspidatum*. The study includes the anti-oxidant, skin-lightening and anti-wrinkle effects in vitro.

Determination of Antioxidant Activity

Skin cells, being near the surface of the body, are bombarded with additional stressors from the environment that fail to reach other cells deep within the body's interior. This increases the volume of oxidative stress present in the skin. Once a free radical touches the cell, the cascade of free radical damage begins. Antioxidants can neutralize free radicals before they touch the cell, as well as stop ongoing interior cellular damage. Many of them get through the initial skin barrier or come from inside the cell itself via cellular metabolism. Antioxidants combining with free radicals upstream can help to prevent a large cascade of damage. In this way, antioxidants can prevent the multiplication of damage seen downstream. Following sections contain the in vitro antioxidant assay reports for 50% RS from *Polygonum cuspidatum* and RSF.

DPPH Radical Scavenging Assay

The free radical scavenging capacity of the test sample was determined using DPPH scavenging assay (Braca et al. 2001). DPPH solution was prepared in 95% methanol. Freshly prepared DPPH solution was taken in test tubes and different concentration of test samples were added and incubated for 20 min. The absorbance was read at 517 nm using a spectrophotometer. Blank was prepared containing the same volume of reaction mixture without any test samples. The percentage of scavenging was calculated using the formula:

% Scavenging=$Ac-As/Ac$×100

Where Ac was the absorbance of the control (blank without extract) and As was the absorbance in the presence of the extract.

Results

Figure 2:
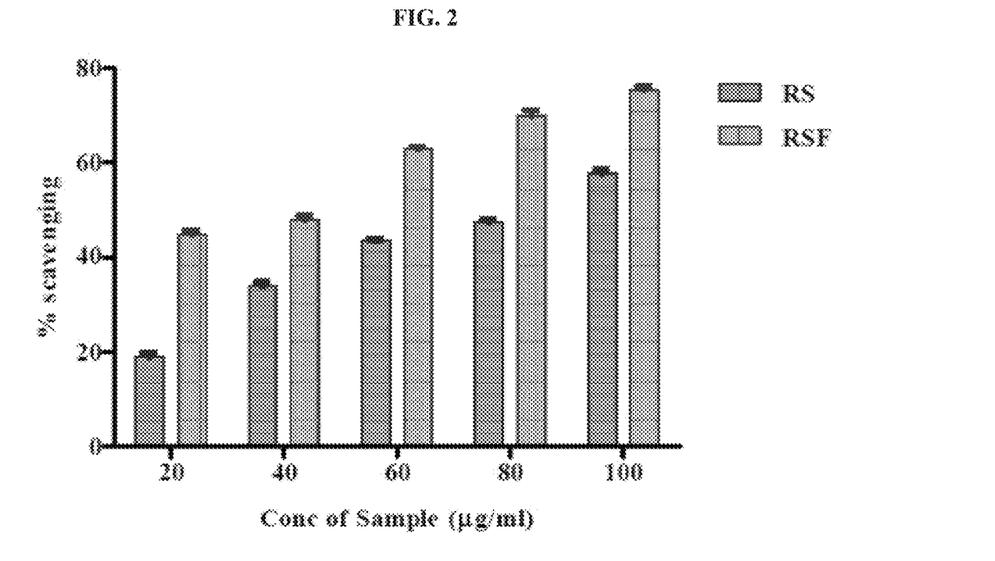
FIG. 2 shows the DPPH scavenging activity of bioenhanced resveratrol.

DPPH radical scavenging is a simple and reliable assay for the determination of antioxidant activity of any given drug/sample. The scavenging activity was more pronounced by RSF as compared to RS (FIG. 2). The percentage inhibition of DPPH radical by RS and RSF were 57.7% and 75.2% respectively at concentration of 100 μg/ml (Table 1).

TABLE 1

DPPH scavenging activity of RS and RSF

| | Absorbance @517 nm | % inhibition | Absorbance @517 nm | % inhibition |
|---|---|---|---|---|
| Blank | 1.963 | | 2.242 | |
| 20 | 1.591 | 18.956 | 1.235 | 44.92 |
| 40 | 1.298 | 33.88 | 1.167 | 47.95 |

TABLE 1-continued

DPPH scavenging activity of RS and RSF

| | Absorbance @517 nm | % inhibition | Absorbance @517 nm | % inhibition |
|---|---|---|---|---|
| 60 | 1.111 | 43.40 | 0.831 | 62.93 |
| 80 | 1.030 | 47.53 | 0.671 | 70.07 |
| 100 | 0.830 | 57.72 | 0.556 | 75.20 |

Example 3—Protective Effect of Bioenhanced Resveratrol Against Hydroxyl Radical Mediated DNA Scission The experiment was conducted using calf thymus DNA (Xican et al. 2013). Briefly, sample was dissolved in ethanol at 1 mg/mL. 50 µl of different concentration of sample was then separately taken into mini tubes followed by addition of 400 µL of phosphate buffer (0.2 mol/L, pH 7.4). Subsequently, 50 µL DNA sodium, 50 µL $H_2O_2$, 50 µL $FeCl_3$ and 50 µL $Na_2$EDTA (1 mmol/L) were added. The reaction was initiated by adding 50 µL ascorbic acid (18 mmol/L) and the total volume of the reaction mixture was adjusted to 800 µL with buffer. After incubation in a water bath at 55° C. for 20 min, the reaction was terminated by adding 250 µL TCA. The color was then developed by addition of 150 µL of TBA and heating in an oven at 105° C. for 15 min. The mixture was cooled and absorbance was measured at 532 nm against the buffer (as blank). The percent protective effect against DNA damage is expressed:

Protective effect %=$(1-A/A_0) \times 100$

Where $A_0$ is the absorbance of the mixture without sample, and A is the absorbance of the mixture with sample.

Results

Figure 3:
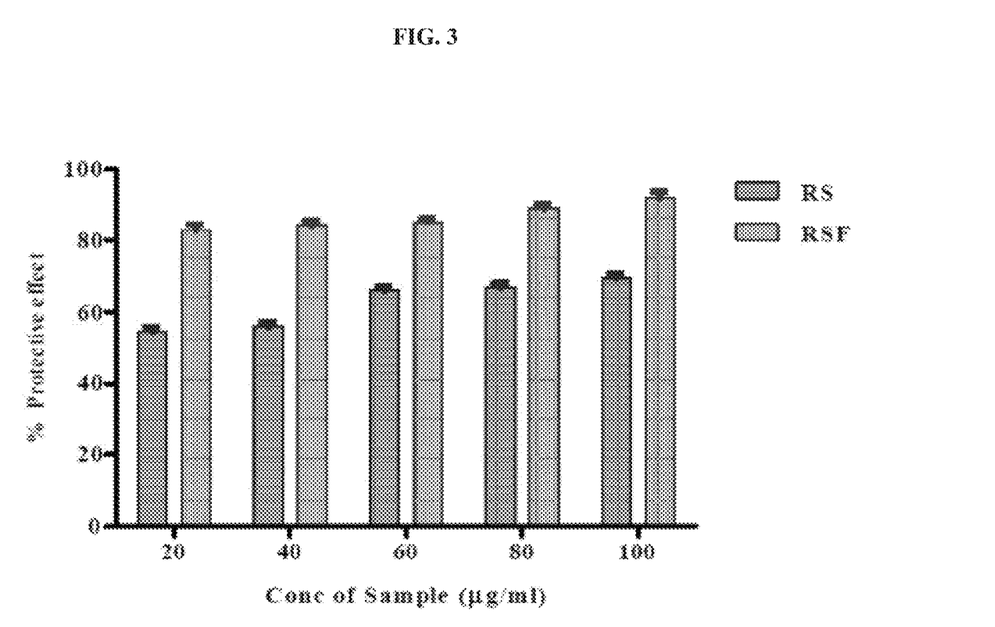
FIG. 3 shows the DNA protective activity of bioenhanced resveratrol.

The DNA damage study is a reliable assay to evaluate the protective role of drug/extract against ROS mediated oxidative stress. Protection of vital biological macromolecules such as nucleic acids is the major mechanism by which the drugs do exert their antioxidant property. In the present study, both test sample RS and RSF showed promising DNA protection against damage induced by Fenton's reagent. Interestingly as compared to RS, RSF was highly effective in retaining the structural integrity of plasmid DNA (i.e., at a concentration as low as 20 µg, DNA protective activity of RS and RSF was found to be 54.62 and 82.98% respectively). At the highest concentrations tested the values were 69.75 and 91.1% for RS and RSF samples respectively (FIG. 3).

TABLE 2

DNA protective activity RS and RSF

| | Absorbance @532 nm | % inhibition | Absorbance @ 532 nm | % inhibition |
|---|---|---|---|---|
| Blank | 0.238 | | 0.235 | |
| 20 | 0.108 | 54.62 | 0.040 | 82.98 |
| 40 | 0.105 | 55.88 | 0.037 | 84.26 |
| 60 | 0.081 | 65.97 | 0.035 | 85.11 |
| 80 | 0.079 | 66.81 | 0.026 | 88.94 |
| 100 | 0.072 | 69.75 | 0.019 | 91.91 |

Example 4—Effects of Bioenhanced Resveratrol in Skin Lightening Activity

In Vitro Anti-Tyrosinase Assay

Tyrosinase is a multifunctional, glycosilated, copper containing oxidase and found exclusively in melanocytes. The enzyme plays a major role in inducing hyperpigmentation of skin in several dermatological disorders thus becoming a therapeutic target for many depigmenting agents. There is growing interest to search for new active tyrosinase inhibitors for skin whitening or antibrowning preparations (Bourin et al. 2002). We have performed the in vitro assay for the tyrosinase enzyme inhibition by RS and RSF.

Reaction mixture contained 100 µl of 0.1 M potassium phosphate buffer, 200 units of tyrosinase enzyme, various concentrations of test sample (20-100 µg/ml) and 5 mM substrate (tyrosine). Extracts were pre-incubated with enzyme for 10 min at 37° C. and reaction was started with the addition of substrate and further incubated for 15 min. In control samples, only potassium phosphate buffer was used instead of extracts. The absorbance was monitored at 475 nm.

Results

Figure 4:
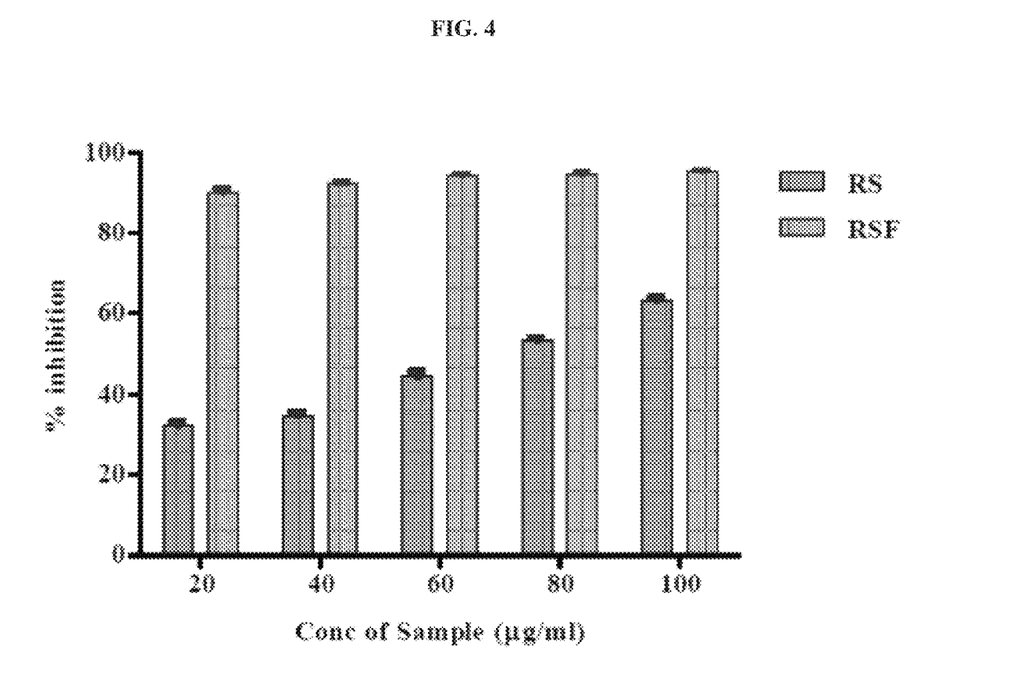
FIG. 4 shows tyrosinase inhibition activity bioenhanced resveratrol.

RS and RSF were tested for tyrosinase inhibitory activity. Above results reveals that RS and RSF showed good inhibitory effect at all the tested concentrations. There was concentration dependent increase in percentage of inhibitory activity. At a higher concentration of 100 µg the maximum inhibitory effect of RS & RSF was found to be 97.74% and 95.40% respectively (FIG. 4).

TABLE 3

Tyrosinase inhibition activity of RS and RSF

| | Absorbance @ 475 nm | % inhibition | Absorbance @ 475 nm | % inhibition |
|---|---|---|---|---|
| Blank | 0.133 | | 0.261 | |
| 20 | 0.090 | 32.33 | 0.026 | 90.04 |
| 40 | 0.087 | 34.59 | 0.020 | 92.34 |
| 60 | 0.074 | 44.36 | 0.015 | 94.25 |
| 80 | 0.062 | 53.38 | 0.014 | 94.64 |
| 100 | 0.049 | 63.16 | 0.012 | 95.40 |

Example 5—Effect of Bioenhanced Resveratrol in the Treatment of Wrinkles

Anti-Elastase Activity (Lee et al. 1999)

Elastase, a member of the chymotrypsin family of proteases, is responsible primarily for the breakdown of elastin, an insoluble elastic fibrous protein that, together with collagen, determines the mechanical properties of connective tissue (Antonicelli et al. 2007). During the recent past a number of studies have investigated the interactions between elastase and its inhibitors (Kim et al. 2007; Masuda et al. 2009). Plant products have drawn significant attention in cosmetic applications due to their limited side effects. We have evaluated here the plausible anti-wrinkle effects of RS and RSF; the comparative results are reported.

Reaction mixture contained 800 µl of 0.2M Tris HCL buffer, 100 µg/ml elastase, various concentrations of test sample and 0.8 mM substrate. Extracts were preincubated with enzyme for 20 min at 25° C. and reaction was started with the addition of substrate. In control only Tris HCL buffer was used instead of extracts. The absorbance was monitored for 20 min at 410 nm.

Results

Figure 5:
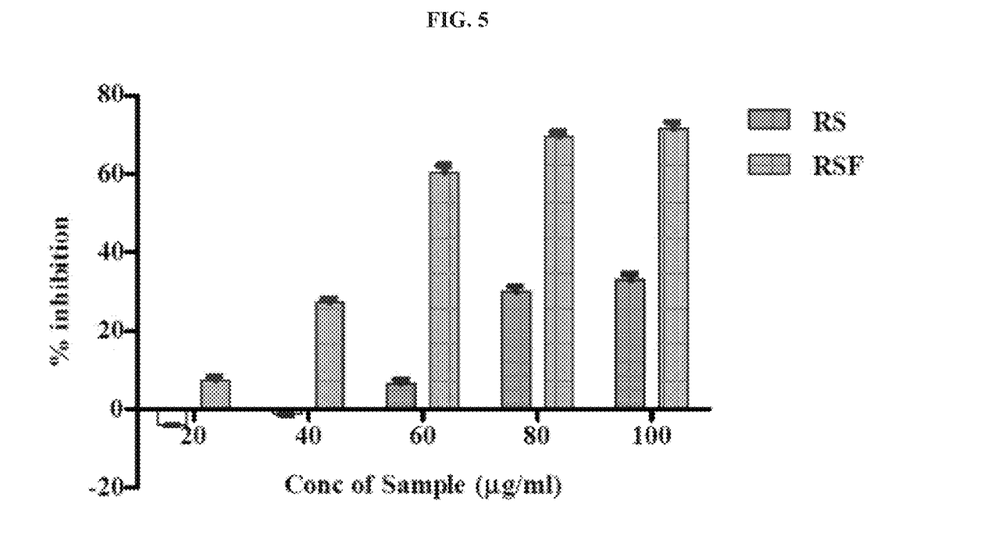
FIG. 5 shows elastase inhibition activity of bioenhanced resveratrol.

The Inhibitory ability of RS and RSF on procine pancreatic elastase is shown in FIG. 5. The test samples were capable of inhibiting elastase in an amount dependent manner. At 100 µg RS and RSF exhibited 32.81 and 71.66% inhibition activity respectively. Above results reveals RSF showed more than a two-fold increase in the inhibitory effect at the highest concentration. RS was not effective in inhibiting elastase activity.

TABLE 4

Elastase inhibition activity of RS and RSF

| | Absorbance @410 nm | % inhibition | Absorbance @ 410 nm | % inhibition |
|---|---|---|---|---|
| Blank | 0.341 | | 0.247 | |
| 20 | 0.355 | −4.11 | 0.229 | 7.29 |
| 40 | 0.345 | −1.17 | 0.180 | 27.13 |
| 60 | 0.319 | 6.45 | 0.098 | 60.32 |
| 80 | 0.239 | 29.91 | 0.075 | 69.34 |
| 100 | 0.229 | 32.84 | 0.070 | 71.66 |

Example 6—Moisturing Effects of Bioenhanced Resveratrol

Various moisturizers claim to make skin look younger, healthier, brighter and more even. They might promise to minimize pores or to tighten and tone skin. Moisturizers affect the appearance of skin by doing three things—fighting dryness, balancing skin tone and improving skin texture. Therefore, the moisturizing effect of RSF was examined in vitro.

Sample Preparation:

The resveratrol sample solution was prepared by mixing with lecithin-base and distilled water in the ratio 3%, lecithin 5% and distilled water 92%. Condition: Temperature 35° C., RH 40%. 1 g of resveratrol sample solution was weighed and added to vessel (3 cm). Samples were weighed 8 hours later. Moisturizing ratio was calculated as follows:

Moisturising Ratio (%)=((Weight at 0 hour−Weight at 8 hour)/Original Weight)×100

Results

Figure 6:
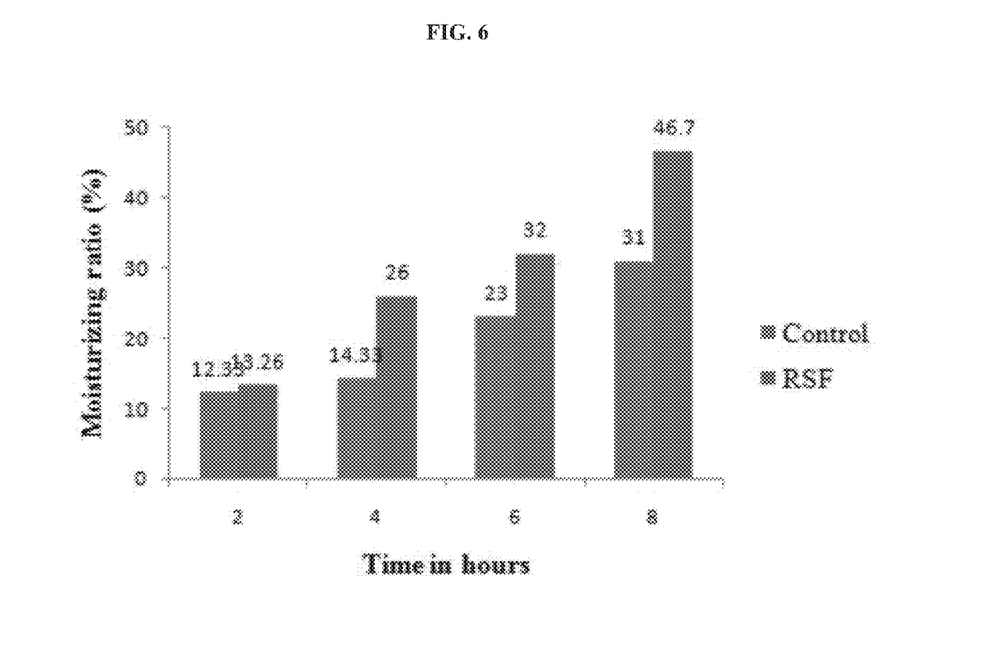
FIG. 6 shows the moisturizing effect of bioenhanced resveratrol.

RSF demonstrated superior moisturizing effect with maximum moisturizing ratio of 46% (FIG. 6). Our study claims that RSF can be exploited as moisturizer to make the skin look younger and brighter.

REFERENCES

1. Antonicelli F, Bellon G, Debelle L, Hornebeck W. Elastin-elastases and inflamm-aging. Curr Topics Develop Biol 2007; 79: 99-155.
2. Athar M, Back J H, Tang X, et al. Resveratrol: a review of preclinical studies for human cancer prevention. Toxicol Appl Pharmacol. 2007; 224: 274-283.
3. Baurin N, Arnoult E, Scior T, Do Q T, Bernard P. Preliminary screening of some tropical plants for anti-tyrosinase activity. J Ethnopharmacol 2002; 82(2-3): 155-8.
4. Bielsalski H K. Polyphenols and inflammation: basic interactions. Current opinion in clinical nutrition and metabolic care. 2007; 10: 724-728.
5. Braca A, de Tommasi N, di Bari L, Pizza C, Politi M, Morelli I. (2001). Antioxidant principles from *Bauhiniatera potensis. J. Nat. Prod.*, 64:892-895
6. Jeandet P. Bessis R, Gautheron B. The Production of resveratrol (3,5,4'-trihydroxystilbene) by Grape Berries in Different Developmental Stages. American J Enol Viti cult. 1991; 42: 41-46.
7. Jenkins G. Molecular mechanisms of skin ageing. Mech Ageing Dev 2002; 123: 801-810.
8. Kim Y H, Kim K S, Han C S, Yang H C, Park S H, Ko K I et al. Inhibitory effects of natural plants of Jeju Island on elastase and MMP-1 expression. Int J Cosmetic Sci 2007; 29: 487-488.
9. Lee K K. Kim J H, cho J J, Choi J D. Inhibitory effects of 150 plant extracts on anti-elastase activity and their anti-inflammatory effects. Int J Cosmet Sci 1999; 21: 71-82
10. Maeda K, Fukuda M. Arbutin: mechanism of its depigmenting action in human melanocyte culture. J pharmacol Exp Ther 1996; 276: 765-769.
11. Masuda M, Murata K, Fukuhama A, Naruto S, Fujita T, Uwaya A et al. Inhibitory effects of constituents of Morindacitrifolia seeds on elastase and tyrosinase. J Nat Med 2009; 63: 267-273.
12. Nishikimi, M, Rao, N A, Yagi, K (1972). The occurrence of superoxide anion in the reaction of reduced phenazinemethosulfate and molecular oxygen. *Biochem. Biophys. Res. Commum.* 46: 849-854.
13. Oyazu M (1986). Studies of product browning reaction: antioxidant activity of producbrowning reaction from glucosamine. Jap. J. Nut. 44: 397-315.
14. Schlotmann K, Kaeten E, Black A F, Damour O, Waldmann-Laue M, Forster T. Cosmetic efficacy claims in vitro using a three-dimensional human skin model. Int J Cos Sci 2001; 23:309-318.
15. Shankar S, Singh G, Srivastava R K. Chemoprevention by resveratrol: molecular mechanisms and therapeutic potentials. Front Biosci. 2007; 12: 4839-4854.
16. SjerobabskiMasnec I, Poduje S. Photoaging. CollAntropol 2008; 32(2): 177-180.
17. Xican Li, Yanping Huang, Dongfeng Chen (2013). Protective Effect against Hydroxyl-induced DNA Damage and Antioxidant Activity of Citrireticulatae Pericarpium. Advanced Pharmaceutical Bulletin. 3(1), 175-181
18. Lee K K, Kim J H, Cho J J, Choi J D (1999): Inhibitory effects of 150 plant extracts on anti-elastase activity and their anti-inflammatory effects. Int J Cosmet Sci; 21: 71-82
19. Narisa Kamkaen, Narong Mulsri and Charoen Treesak (2007). Screening of some tropical vegetables for Anti-tyrosinase activity Thai Pharmaceutical and Health Science Journal. Vol. 2 No. 1.

The invention claimed is:

1. A resveratrol composition having enhanced systemic bioavailability, the composition comprising resveratrol, lecithin and a comestible oil, wherein the resveratrol, lecithin and the comestible oil are present in a ratio of about 50:1:1 respectively, wherein the lecithin and comestible oil increase the systemic bioavailability of the resveratrol at least three-fold when orally administered to a subject compared to the bioavailability of the resveratrol in the absence of the lecithin and the comestible oil.

2. The composition of claim 1, wherein the comestible oil is selected from the group consisting of grape seed oil, jojoba oil, soybean oil, almond oil, avocado oil, petrolatum oil, vegetable oil, peanut oil, canola oil, flax seed oil, palm kernel oil, coconut oil, olive oil, or a combination thereof.

3. The composition of claim 1, wherein the comestible oil is grape seed oil.

4. The composition of claim 1, wherein the lecithin is sunflower lecithin.

5. The composition of claim 1, wherein the composition comprises 50% resveratrol, 1% lecithin and 1% comestible oil.

6. The composition of claim 1, wherein the composition is in the form of a powder, pill, tablet, pellet, capsule, thin film, solution, spray, syrup, linctus, lozenge, pastille, chewing gum, paste, suspension, solution, vapor, emulsion, ointment, cream, lotion, liniment, gel, drop, buccal patch, bead, gummy, or sol.

7. A method for treating a skin condition in a subject in need thereof comprising orally administering to the subject a resveratrol composition having enhanced systemic bioavailability wherein the composition comprises resveratrol, lecithin and a comestible oil in a ratio of about 50:1:1, wherein the lecithin and comestible oil increase the systemic bioavailability of the resveratrol at least three-fold when administered to the subject orally compared to the systemic bioavailability of the resveratrol in the absence of the lecithin and comestible oil, and wherein administering the composition treats the skin condition in the subject.

8. The method of claim 7, wherein the skin condition is wrinkles or hyperpigmentation.

9. The method of claim 7, wherein the comestible oil is selected from the group consisting of grape seed oil, jojoba oil, soybean oil, almond oil, avocado oil, petrolatum oil, vegetable oil, peanut oil, canola oil, flax seed oil, palm kernel oil, coconut oil, olive oil or a combination thereof.

10. The method of claim 7, wherein the comestible oil is grape seed oil.

11. The method of claim 7, wherein the lecithin is sunflower lecithin.

12. The method of claim 7, wherein the composition comprises 50% resveratrol, 1% lecithin and 1% comestible oil.

13. The method of claim 7, wherein the composition is in the form of a powder, pill, tablet, pellet, capsule, thin film, solution, spray, syrup, linctus, lozenge, pastille, chewing gum, paste, suspension, solution, vapor, emulsion, ointment, cream, lotion, liniment, gel, drop, topical buccal patch, bead, gummy, or sol.

* * * * *